United States Patent [19]

Feier et al.

[11] Patent Number: 4,726,220

[45] Date of Patent: Feb. 23, 1988

[54] METHOD OF AND APPARATUS FOR MEASURING RHEOLOGICAL CHARACTERISTICS OF SUBSTANCES

[75] Inventors: Markus Feier, Otelfingen; Georg Zemp, Zürich, both of Switzerland

[73] Assignee: Contraves AG, Zürich, Switzerland

[21] Appl. No.: 936,504

[22] Filed: Dec. 1, 1986

[30] Foreign Application Priority Data

Dec. 13, 1985 [CH] Switzerland .................. 05310/85

[51] Int. Cl.$^4$ ........................................... G01N 11/14
[52] U.S. Cl. .................................................. 73/59
[58] Field of Search ...................................... 73/59, 60

[56] References Cited

U.S. PATENT DOCUMENTS

| | | | |
|---|---|---|---|
| 3,343,405 | 9/1967 | Gilinson et al. | 73/59 |
| 3,545,257 | 12/1970 | Zemp et al. | 73/59 |
| 3,667,286 | 6/1972 | Kaufman et al. | 73/59 |
| 4,148,216 | 4/1979 | Do et al. | 73/59 |

FOREIGN PATENT DOCUMENTS

| | | | |
|---|---|---|---|
| 684935 | 12/1952 | United Kingdom | 73/59 |
| 433381 | 6/1975 | U.S.S.R. | 73/59 |
| 702269 | 12/1979 | U.S.S.R. | 73/59 |

Primary Examiner—Stewart J. Levy
Assistant Examiner—Joseph W. Roskos
Attorney, Agent, or Firm—Werner W. Kleeman

[57] ABSTRACT

The viscometer comprises a measuring element suspended on a torsion wire and immersed in a substance to be tested contained in a measurement vessel. The measurement vessel with the therein contained substance is driven by a first drive member. A second drive member as well as a measuring system are arranged on a shaft between the torsion wire and the measuring element. A signal transducer prescribes or sets a predetermined amount of torque for the second drive member. The predetermined amount of torque corresponds to a predetermined shear stress characteristic of the substance to be measured. A predetermined angular deflection or angular velocity is applied to the first drive member through a regulation connection arranged between the measuring system and the first drive member. The viscometer is, due to its high accuracy, particularly advantageous for applications in low viscosity ranges of structurally viscous substances.

12 Claims, 2 Drawing Figures

METHOD OF AND APPARATUS FOR MEASURING RHEOLOGICAL CHARACTERISTICS OF SUBSTANCES

BACKGROUND OF THE INVENTION

The present invention broadly relates to a new and improved method of and apparatus for measuring rheological characteristics of substances in a rotary viscometer.

In its more specific aspects the present invention relates to a new and improved construction of a rotary viscometer in which a measuring or measurement element or probe immersed in a measurement or measuring vessel containing the substance to be investigated, and in which either the measurement vessel or measuring element is turned or angularly displaced about a predetermined vertical axis by means of an associated drive member. At least the measureing or measurement vessel and the measuring or measurement element conjointly constitute a measuring arrangement.

In other words, the viscometer of the present invention is of the type comprising a first drive member such as an electric motor, a measurement or measuring vessel driven by the first drive member, a measurement or measuring element or probe arranged in free suspension in the measurement vessel by means of a torsion wire and a shaft, a correspondingly associated measurement or measuring system and a second drive member associated with the shaft. The second drive member is operatively connected to a reference value transducer or signal transmitter via a signal conductor. A regulation connection connects the measuring system with the first drive member for selectively regulating the angular velocity or angular displacement of the measurement vessel.

Generally speaking, the method of the present invention is for measuring the rheological properties of a substance in a rotary viscometer and comprises the steps of: depositing the substance to be measured in a measurement vessel; immersing a measurement or measuring element or probe in the substance in the measurement vessel such that the measurement vessel and the measuring element or probe conjointly form a measurement arrangement; and rotating or turning a selected one of the measurement vessel and the measuring element or probe about a substantially vertical axis by means of a therewith associated drive member.

A viscometer of this general type is, for instance, described in the German Petty Pat. No. 7,637,450, wherein determination of the flow or viscosity curve is achieved by incrementally changing the rotational speed of a geared motor driving the measuring or measurement vessel and by determining the amount of torque exerted on the measuring body and its suspension by the substance to be measured. The incremental change of the rotational speed or the rotational deflection of the measuring vessel will lead to inaccurate or incomplete determination of the flow or viscosity curve for certain structurally viscous substances.

As a function of structurally viscous characteristics, particularly within low viscosity ranges, e.g. in rheological blood tests, the characteristics of certain substances suddenly and irreversibly change when exceeding a certain predetermined rotary speed or angular velocity (shear rate), such that a given measurement cannot be repeated on the same sample for determining the exact crossover value or flow limit of the substance. Furthermore, the incremental change of the rotational speed of the measurement or measuring vessel is relatively inaccurate with equipment generally available at reasonable costs, such that even for small rotational speed increments it is difficult to determine the exact speed corresponding to a given torque (shear stress) correlated to the specific properties of the substance to be measured.

SUMMARY OF THE INVENTION

Therefore, with the foregoing in mind, it is a primary object of the present invention to provide a new and improved method of and apparatus for rheometry which do not exhibit the aforementioned drawbacks and shortcomings of prior art constructions.

A further significant object of the present invention is to provide a new and improved method of and apparatus for more accurate rheometric viscosity measurements, in particular for low viscosity values of structurally viscous substances which eliminate the aforementioned drawbacks and shortcomings by means of improved regulation and structural features, and which are utilizable in the range extending to the flow or viscosity limit of such substances, thus providing more accurate results, in particular for substances with low viscosity values.

In order to implement these and still further objects of the invention, which will become more readily apparent as the description proceeds, the apparatus of the present invention for measuring rheological characteristics of a structurally viscous substance is manifested by the features that it comprises a rotary viscometer having a measuring or measurement element or probe immersed in a measuring or measurement vessel containing the substance to be measured, and either the measurement vessel or the measuring element or probe is angularly displaced or turned about a predetermined axis by means of an associated drive member. At least the measuring or measurement vessel and the measuring or measurement element or probe conjointly constitute a measuring arrangement.

The method of the present invention for measuring rheological characteristics of substances is manifested by the features that it comprises the steps of: applying a predetermined torque value to a supplementary second drive member which is operatively connected to the measuring element of the measuring arrangement, causing the measuring element of this measuring arrangement to slightly angularly deflect from its zero or starting position; measuring the rotation angle or angular displacement thus generated; employing this angular displacement to generate a measurement or control signal; conducting the measurement or control signal via a regulating circuit to the first drive member for returning the angularly deflected or displaced measuring element of the measuring arrangement as well as the second drive member back to the zero or starting position; and employing a deflection value of the first drive member for determining the rheological characteristics of the substance.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings there have been generally

DETAILED DESCRIPTION OF THE PREFERRED EMBODIMENTS

Figure 1:
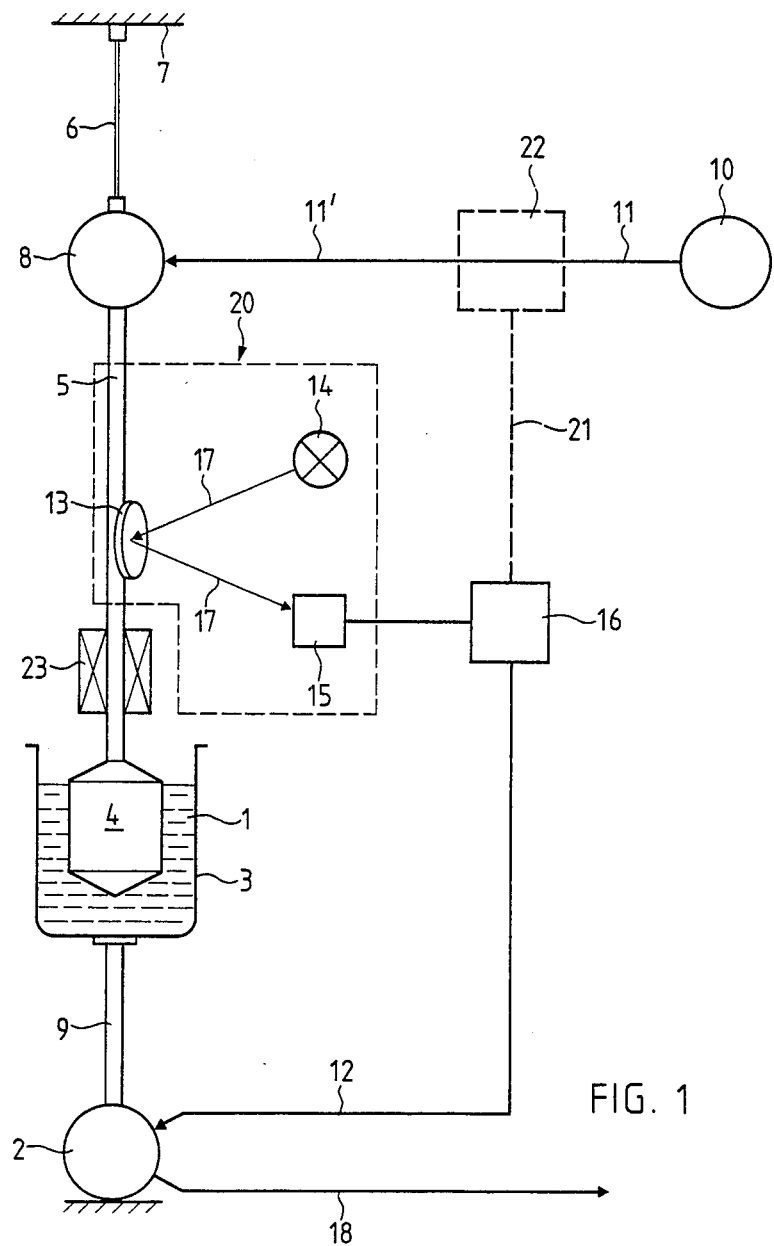
FIG. 1 shows a schematic depiction of a rotary viscometer in accordance with the teachings of the invention.

Describing now the drawings it is to be understood that to simplify the showing thereof only enough of the structure of the apparatus for measuring the rheological characteristics of a substance has been illustrated therein as is needed to enable one skilled in the art to readily understand the underlying principles and concepts of the present invention. The substance 1 which is to be tested is filled into a measuring or measurement vessel 3 which is operatively connected by a first shaft 9 to a first drive member 2, such as an electric motor. Subsequently a, for instance, cylindrical measuring or measurement element or probe 4 mounted to a second shaft 5 is immersed into the substance 1. The elements 2, 3, 4 and 9 conjointly constitute a measuring or measurement arrangement. In order to avoid axial bearing friction the measuring element 4 and the second shaft 5 serving for torque measurements are both suspended on a torsion wire 6 or equivalent structure. The torsion wire 6 is fastened at one end to a housing 7 partially schematically depicted in FIG. 1 and otherwise not herein shown in detail.

In contradistinction to the present state of the art, a second drive member 8, for instance a torque motor, is arranged between the torsion wire 6 and the second shaft 5. A reference or set torque value for the second drive member 8 is prescribed by a nominal or reference or set value transducer 10. The reference or set torque value essentially corresponds to a predetermined shear stress or a predetermined viscosity value, respectively, of the test substance 1. The first drive member 2 generates a counter-value for countering the angular displacement or rotational speed induced by the second drive member 8, such that a corresponding flow or viscosity diagram may be recorded with a suitable, herein not depicted recording instrument or the like. For this purpose the first drive member 2 is regulated or controlled by means of a regulation or control connection 12 between the first drive member 2 and a measuring system 20 by utilizing a measurement value signal formed by angular displacement induced by the second drive member 8 in order to produce the aforementioned counter-value such that the two torque values of both drive members 8 and 2 compensate each other. Thus measurement can be accomplished substantially without torsion within the elements 5 and 6.

For adjusting the torsion value to a zero position in which the torque values of both driving members 2 and 8 are mutually compensated, various kinds of measuring systems 20 are suitable—however, it is preferable to use an optical reflecting system or arrangement such as a mirror system in order to obtain the high accuracy required.

The measuring system 20 essentially comprises a reflector or mirror 13 fastened to the second shaft 5, a stationary light source 14 mounted within the housing 7 of the viscometer and a photoelectric sensor 15 connected to an amplifier 16. In dependence of the deviation from a torsion-free zero position of a light beam 17 originating from the stationary light source 14 and reflected by the mirror 13, the photoelectric sensor 15 controls via the amplifier 16 the electric current fed to the first drive member 2 via the regulation or control connection 12. The angular displacement or the rotational speed caused by the turning of the measuring or measurement vessel 3 can be detected at the first drive member 2 via a signal line 18. For this purpose the first drive member 2 is preferably configured as a stepping motor.

To avoid falsification of the measurement result due to the spring constant of the torsion wire 6, there is connected, according to a variant embodiment of this invention, an electrical circuit 22 within the signal line 11, 11'. The electrical circuit 22 is connected to the amplifier 16 and the measuring system 20 by means of a signal line 21 herein depicted as a dashed line. The electrical circuit 22 is fed a correcting signal via the signal line 21 as a function of the true deflection value of angular displacement of the second shaft 5.

FIG. 1 schematically shows a radial bearing 23 for journaling the second shaft 5. However, in accordance with the teachings of the invention it is possible to omit this radial bearing 23 whenever using the viscometer for substances with relatively low viscosity, in order to render measurement without the influence of frictional forces possible. For investigating relatively highly viscous substances, or in cases in which centering of the shaft 5 or of the measuring element 4 by the second drive member 8 is not sufficient, the radial bearing 23 can be made exchangeable conjointly with the measuring element 4 and the second shaft 5.

Figure 2:
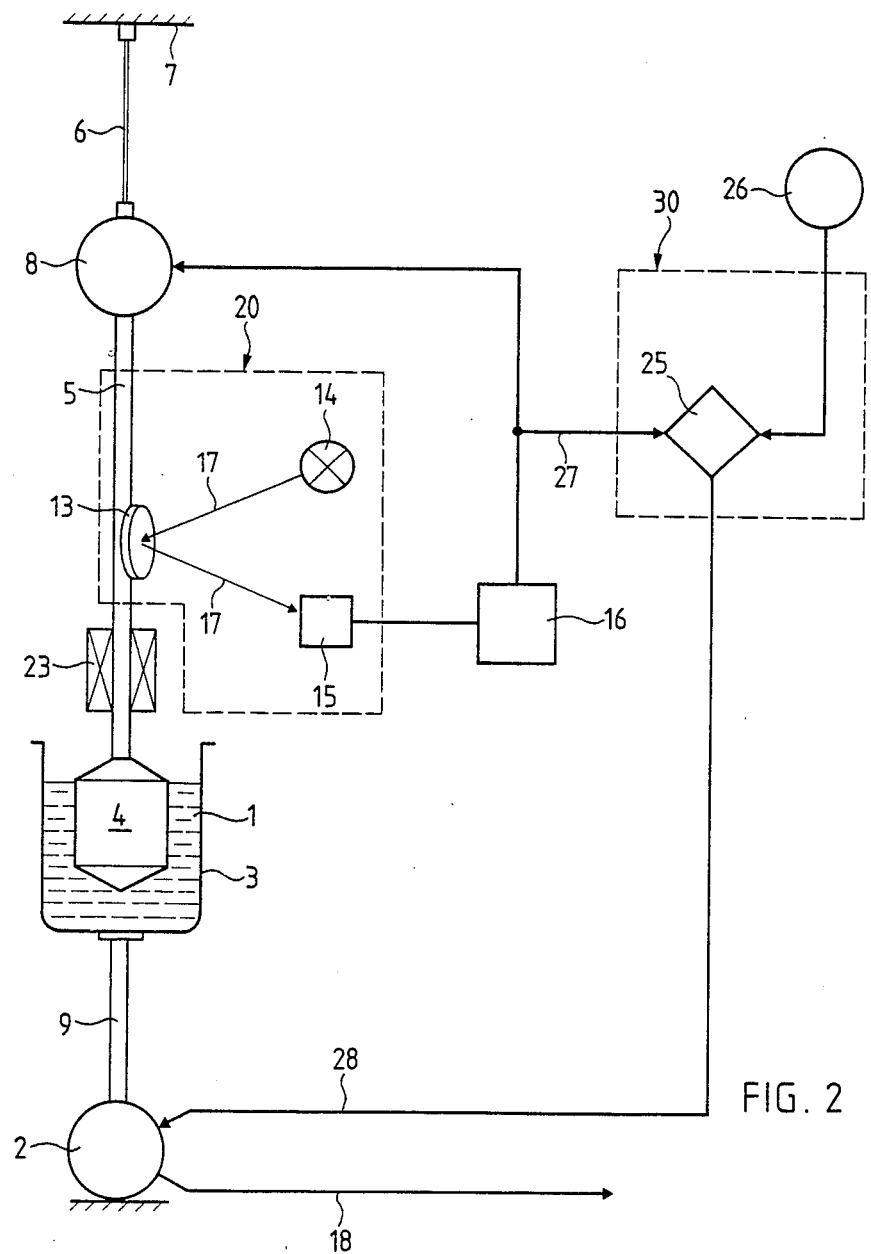
FIG. 2 shows a schematic depiction of a further embodiment of a viscometer.

The embodiment according to FIG. 2 differs from the previously described embodiment by the provision of an additional control means 30 including an electrical comparator element or comparator 25 to which there is fed a nominal or reference or set value signal provided by a nominal or reference or set value transducer 26. This nominal or reference or set value signal is compared with an actual value signal derived from the second drive member 8 and the measuring system 20. This actual value signal is delivered via a signal line 27 to the electrical comparator element 25. The electrical comparator element 25 is connected with the first drive member 2 via a regulation or control connection 28 to control the first drive member 2 such that any deviations between the actual value and the nominal or reference or set value are compensated or adjusted to zero. In this embodiment as well, the angular displacement or, respectively, the rotational speed of the drive member 2 generates the value to be measured after the shear stress has been preset by the torque value at the drive member 8.

It will be understood that the deflection from the zero position of one measuring component of the measuring arrangement to the other is relatively small and lies in the order of magnitude below one angular degree.

While there are shown and described present preferred embodiments of the invention, it is to be distinctly understood that the invention is not limited thereto, but may be otherwise variously embodied and practiced within the scope of the following claims.

Accordingly, What we claim is:

1. A method for measuring the rheological properties of a substance by means of a rotary viscometer having a measuring element and a measurement vessel, comprising the steps of:

immersing the measuring element into a substance to be measured contained in the measurement vessel;

turning a first member of a pair comprising the measurement vessel and the measuring element from a starting position about a predetermined axis to impart a rotational angular displacement to said turned first member of the pair comprising the measurement vessel and the measuring element;

measuring said rotational angular displacement thus imparted;

forming a measurement value signal from said measured rotational angular displacement;

utilizing said measurement value signal for turning a second member of the pair comprising the measurement vessel and the measuring element in response to said measurement value signal and thereby returning said first member of the pair comprising the measurement vessel and the measuring element back to said starting position;

determining a counter-value associated with said second member and the return of said first member into said starting position; and employing said counter-value for determining the rheological properties of the substance.

2. The method as defined in claim 1 wherein:

said step of turning said first member of the pair comprising the measurement vessel and the measuring element entails turning the measuring element from its starting position; and said step of turning said second member entailing the step of turning the measurement vessel.

3. A method for measuring the rheological properties of a substance by means of a rotary viscometer measurement arrangement having a measuring element and a measurement vessel, comprising the steps of:

immersing the measuring element in a substance to be measured contained in the measurement vessel;

the measuring element and the measurement vessel each defining a respective measurement component of the measurement arrangement;

applying a predetermined torque to a drive member drivingly connected to one measurement component of said measurement components and thereby moving said one measurement component out of a zero position relative to one other measurement component of said measurement components by a rotational angular displacement;

measuring said rotational angular displacement thus generated;

forming a measurement value signal from said measured rotational angular displacement;

rotationally angularly displacing said other measurement component, in response to said measurement value signal, by means of a further drive member via a regulating circuit and thereby producing a return rotational angular displacement of said rotationally angularly displaced one measurement component and said drive member to said zero position; and employing a measured value related to said return rotational angular displacement produced by said further drive member for determining the rheological properties of the substance.

4. A method for measuring the rheological properties of a substance by means of a rotary viscometer measurement arrangement having a measuring element and a measurement vessel, comprising the steps of:

immersing the measuring element in a substance to be measured contained in the measurement vessel;

the measuring element and the measurement vessel each defining a respective measurement component of the measurement arrangement;

applying a predetermined torque to a drive member such that one measurement component of said respective measurement components operatively connected to said drive member is moved out of a zero position relative to one other measurement component of said respective measurement components by the amount of an angular displacement;

measuring said angular displacement thus generated;

forming a measurement value signal from said measured angular displacement;

conducting said measurement value signal to a further drive member via a regulating circuit for producing a return angular displacement to serve for returning said angularly displaced one measurement component and said drive member to said zero position;

employing the value of said return angular displacement produced by said further drive member for determining the rheological properties of the substance; and employing said measurement value signal formed from said angular displacement for regulating a torque applied by said further drive member to the measurement vessel.

5. A method for measuring the rheological properties of a substance by means of a rotary viscometer measurement arrangement having a measuring element and a measurement vessel, comprising the steps of:

immersing the measuring element in a substance to be measured contained in the measurement vessel;

the measuring element and the measurement vessel each defining a respective measurement component of the measurement arrangement;

applying a predetermined torque to a drive member such that one measurement component of said respective measurement components operatively connected to said drive member is moved out of a zero position relative to one other measurement component of said respective measurement components by the amount of an angular displacement;

measuring said angular displacement thus generated;

forming a measurement value signal from said measured angular displacement;

conducting said measurement value signal to a further drive member via a regulating circuit for producing a return angular displacement to serve for returning said angularly displaced one measurement component and said drive member to said zero position;

employing the value of said return angular displacement produced by said further drive member for determining the rheological properties of the substance; and employing said measurement signal formed from said angular displacement for regulating an angular velocity of said further drive member.

6. A method of measuring rheological properties of a substance by means of a rotary viscometer, comprising the steps of:

immersing a measuring probe in a substance to be measured contained in a measurement vessel;

applying a reference torque to a drive member operatively connected to one measuring component of the group including said measuring probe and said measurement vessel and thereby moving said one measuring component out of a zero position relative to one other measuring component of the group including said measuring probe and said measurement vessel by rotational angular displacement;

measuring said rotational angular displacement;

forming from said measured rotational angular displacement a measurement signal having a magnitude indicative of said measured rotational angular displacement;

rotationally angularly displacing, in response to said measurement signal, through a regulating circuit and a further drive member said other measurement component through an opposite rotational angular displacement and thereby returning said angularly displaced one measuring component and said drive member operatively connected thereto to said zero position; and employing a measured value related to said opposite rotational angular displacement produced by said further drive member for determining the rheological properties of the substance.

7. A rotary viscometer for measuring rheological properties of a substance, comprising:
a first drive member;
a measurement vessel operatively associated with said first drive member and for accommodating a substance to be investigated;
a measuring element freely suspended in said measurement vessel by means of a torsion wire and a shaft;
a measuring system operatively associated with said shaft;
a second drive member operatively associated with said shaft;
a reference value transducer;
a signal conductor operatively connecting said reference value transducer to said second drive member in order to apply a reference torque to said second drive member in the presence of the substance to be investigated;
said measuring element assuming a starting position in the absence of said reference torque and a rotationally angularly displaced position in the presence of said reference torque;
said measuring system containing detection means responsive to the rotational angular displacement of said measuring element and producing a measurement value signal indicative of the rotational angular position of said measuring element;
a regulating connection responsive to said measurement value signal and connecting said measuring system with said first drive member and
said first drive member, under the control of said regulating connection, rotationally angularly displacing said measurement vessel in an opposite rotational angular direction as compared to said measuring element and thereby returning said measuring element into said starting position.

8. The rotary viscometer as defined in claim 7, wherein:
said measuring system comprises:
a mirror arranged on said shaft;
a light source cooperating with said mirror;
said detection means containing a photoelectric sensor cooperating with said light source via said mirror; and
said measuring system being operatively connected with an amplifier.

9. The rotary viscometer as defined in claim 7, further including:
control means comprising an electrical comparator element for comparing a reference value to an actual value; and
said control means connecting said first drive member to said second drive member and said measuring system.

10. The rotary viscometer as defined in claim 7, further including:
exchangeable radial bearing means for guiding said shaft; and
said exchangeable radial bearing means being exchangeable conjointly with said shaft for selectively operating the rotary viscometer with an unjournaled shaft.

11. A rotary viscometer for measuring rheological properties of a substance, comprising:
a first drive member;
a measurement vessel operatively associated with said first drive member;
a measuring element freely suspended in said measurement vessel by means of a torsion wire and a shaft;
a measuring system operatively associated with said shaft;
a second drive member operatively associated with said shaft;
a reference value transducer;
a signal conductor operatively connecting said reference value transducer to said second drive member;
a regulating connection connecting said measuring system with said first drive member for regulating angular displacement of said measurement vessel; and
a compensating circuit provided in said signal conductor for prescribing a predetermined torque for said second drive member for compensating the spring action of said torsion wire.

12. A rotary viscometer, comprising:
a measurement vessel for accommodating a substance to be investigated;
a first drive member for said measurement vessel;
a first shaft operatively connecting said first drive member to said measurement vessel;
a housing;
a torsion wire attached to said housing;
a second shaft freely suspended from said housing by said torsion wire;
a measuring probe freely suspended within said measurement vessel by means of said freely suspended second shaft and assuming a starting position and a rotationally angularly displaced position;
a measuring system appropriately associated with said second shaft;
said measuring system containing detection means responsive to the rotational angular displacement of said measuring probe and producing a measurement value signal indicative of the rotational angular position of said measuring probe;
a second drive member operatively associated with said second shaft;

a reference value generator;

a signal conductor for operatively connecting said reference value generator to said second drive member in order to apply a reference torque to said second drive member and displace said measuring probe into said rotationally angularly displaced position in the presence of the substance to be investigated;

a regulating conductor responsive to said measurement value signal and connecting said measuring system to said first drive member; and said first drive member, under the action of said regulating connection, rotationally angularly displacing said measurement vessel in an opposite rotational angular direction as compared to said measuring probe and thereby returning said measuring probe into said starting position due to the presence of the substance to be investigated.

* * * * *